US012779145B2

(12) United States Patent
Milford et al.

(10) Patent No.: US 12,779,145 B2
(45) Date of Patent: Nov. 3, 2026

(54) DELIVERY DEVICES AND METHODS FOR SURGICAL SUBSTANCES

(71) Applicant: GYRUS ACMI, INC., Westborough, MA (US)

(72) Inventors: Jordan N. Milford, Bethlehem, PA (US); Joey Magno, Dudley, MA (US); Charles A. Baker, Rogers, MN (US)

(73) Assignee: Gyrus ACMI, Inc., Westborough, MA (US)

( * ) Notice: Subject to any disclaimer, the term of this patent is extended or adjusted under 35 U.S.C. 154(b) by 936 days.

(21) Appl. No.: 18/047,015

(22) Filed: Oct. 17, 2022

(65) Prior Publication Data

US 2023/0131550 A1 Apr. 27, 2023

Related U.S. Application Data

(60) Provisional application No. 63/269,069, filed on Mar. 9, 2022, provisional application No. 63/262,850, filed on Oct. 21, 2021.

(51) Int. Cl.
*A61M 13/00* (2006.01)
*A61B 17/12* (2006.01)

(52) U.S. Cl.
CPC ....... *A61M 13/00* (2013.01); *A61B 17/12181* (2013.01); *A61B 2017/12004* (2013.01); *A61M 2205/3331* (2013.01)

(58) Field of Classification Search
CPC .......... A61M 13/00; A61M 2205/3331; A61M 31/00; A61M 2205/3334;
(Continued)

(56) References Cited

U.S. PATENT DOCUMENTS

| | | | |
|---|---|---|---|
| 2,717,804 | A | 9/1955 | White, Jr. |
| 3,633,828 | A | 1/1972 | Larson |

(Continued)

FOREIGN PATENT DOCUMENTS

| | | | |
|---|---|---|---|
| CN | 85108663 | A | 6/1987 |
| CN | 101106946 | A | 1/2008 |

(Continued)

OTHER PUBLICATIONS

"Chinese Application Serial No. 202211285624.3, Response filed Oct. 28, 2024 to Office Action mailed Apr. 29, 2024", w english claims, 18 pgs.

(Continued)

*Primary Examiner* — Bhisma Mehta
*Assistant Examiner* — Marissa Taylor
(74) *Attorney, Agent, or Firm* — Schwegman Lundberg & Woessner, P.A.

(57) ABSTRACT

A clotting agent delivery system comprises a frame, a passageway extending along the frame, a discharge opening connected to the passageway, a clotting agent reservoir fluidly connected to the passageway to hold a clotting agent substance, a valve in the passageway to control flow of the substance through the passageway, and an actuator to allow propellent to flow into the passageway, wherein the valve and clotting agent reservoir cooperate to provide clotting agent substance to the discharge opening at constant pressure using the propellant. A method for delivering a clotting agent comprises inserting a delivery catheter into an anatomic area, coupling a clotting agent delivery system to the delivery catheter, the clotting agent delivery system having a reservoir of a clotting agent, operating a valve to release propellant for propelling the clotting agent, and conveying the propellant and the clotting agent to the delivery catheter at a constant pressure.

18 Claims, 8 Drawing Sheets

(58) Field of Classification Search
CPC ........ A61M 2205/3341; A61M 5/2046; A61M 5/30; A61M 39/00; A61M 39/22; A61M 39/24; A61B 17/12181; A61B 2017/12004; B65D 83/141; B05B 1/3046; B05B 12/085; B05B 7/00; B05B 4/14; B05B 7/1463
See application file for complete search history.

(56) References Cited

U.S. PATENT DOCUMENTS

| | | | | | |
|---|---|---|---|---|---|
| 4,450,858 | A * | 5/1984 | Acomb | G05D 16/0663 137/484.8 |
| 4,501,273 | A | 2/1985 | Mcginnis | |
| 4,546,905 | A | 10/1985 | Nandagiri et al. | |
| 5,105,983 | A | 4/1992 | Sancoff et al. | |
| 5,284,299 | A | 2/1994 | Medlock | |
| 5,454,408 | A * | 10/1995 | DiBella | F04B 9/1176 141/47 |
| 5,954,696 | A | 9/1999 | Ryan | |
| 9,101,744 | B2 | 8/2015 | Ducharme | |
| 9,839,772 | B2 | 12/2017 | Ducharme | |
| 10,806,853 | B2 | 10/2020 | Gittard | |
| 11,052,412 | B2 | 7/2021 | Becker et al. | |
| 2003/0181917 | A1 | 9/2003 | Gertner | |
| 2005/0229985 | A1 | 10/2005 | Saxenfelt | |
| 2008/0214989 | A1 | 9/2008 | Kawata | |
| 2010/0305505 | A1* | 12/2010 | Ducharme | A61M 37/00 604/118 |
| 2015/0094649 | A1 | 4/2015 | Gittard | |
| 2020/0100986 | A1 | 4/2020 | Pic et al. | |
| 2021/0107728 | A1* | 4/2021 | Nasr | B65D 83/38 |

FOREIGN PATENT DOCUMENTS

| | | | |
|---|---|---|---|
| CN | 203539818 | U | 4/2014 |
| CN | 104520198 | A | 4/2015 |
| CN | 105792869 | A | 7/2016 |
| CN | 109496159 | A | 3/2019 |
| CN | 109803709 | A | 5/2019 |
| CN | 111870311 | A | 11/2020 |
| CN | 115998934 | | 4/2023 |
| CN | 117900051 | A | 4/2024 |
| DE | 102022127691 | | 4/2023 |
| EP | 1820455 | | 8/2007 |
| IN | 572618 | B | 10/2025 |
| JP | 3007447 | | 1/1993 |
| JP | 3007447 | U | 2/1995 |
| JP | 2013523336 | | 6/2013 |
| JP | 2016063919 | A | 4/2016 |
| JP | 2016538895 | A | 12/2016 |
| JP | 7641259 | | 2/2025 |
| JP | 7641259 | B2 | 2/2025 |
| TW | 201231117 | A | 8/2012 |
| WO | 03070110 | | 8/2003 |
| WO | 2006061883 | | 6/2006 |
| WO | WO-2012026963 | A2 | 3/2012 |
| WO | WO-2015050814 | A2 | 4/2015 |

OTHER PUBLICATIONS

"Chinese Application Serial No. 202211285624.3, Office Action mailed Jan. 8, 2025", W English Translation, 13 pgs.
"Japanese Application Serial No. 2022-168501, Response filed Dec. 12, 2023 to Notification of Reasons for Rejection mailed Oct. 16, 2023", w english claims, 14 pgs.
"Indian Application Serial No. 202244060467, First Examination Report mailed Jan. 16, 2024", 7 pgs.
Khoshmohabat, Hadi, et al., "Overview of Agents Used for Emergency Hemostasis", Trauma Mon. Feb. 2016; 21(1): e26023, (2016), 6 pgs.
"Indian Application Serial No. 202244060467, Response filed Jul. 16, 2024 to First Examination Report mailed Jan. 16, 2024", w claims, 27 pgs.
"Japanese Application Serial No. 2022-168501, Response filed Sep. 18, 2024 to Notification of Reasons for Refusal mailed Mar. 18, 2024", w english claims, 10 pgs.
"Chinese Application Serial No. 202211285624.3, Decision of Rejection mailed Oct. 11, 2025", w/ English translation, 10 pgs.
"Chinese Application Serial No. 202211285624.3, Office Action mailed Jun. 30, 2025", w/ English Translation, 13 pgs.
"Chinese Application Serial No. 202211285624.3, Response filed May 8, 2025 to Office Action mailed Jan. 8, 2025", w/ english claims, 16 pgs.
"Chinese Application Serial No. 202211285624.3, Response filed Aug. 29, 2025 to Office Action mailed Jun. 30, 2025", w/ claims, 19 pgs.
"Indian Application Serial No. 202244060467, First Examination Report mailed Sep. 16, 2025", 3 pgs.
"Chinese Application Serial No. 202211285624.3, Office Action mailed Apr. 29, 2024", w/ English Translation, 23 pgs.
"Japanese Application Serial No. 2022-168501, Notification of Reasons for Refusal mailed Mar. 18, 2024", w/ English translation, 15 pgs.
"Japanese Application Serial No. 2022-168501, Notification of Reasons for Rejection mailed Oct. 16, 2023", W English Translation, 16 pgs.
"Japanese Application Serial No. 2025-26933, Notification of Reasons for Rejection mailed Mar. 10, 2026", W/English Translation, 8 pgs.
"Japanese Application Serial No. 2025-26933, Response filed May 14, 2026 to Notification of Reasons for Rejection mailed Mar. 10, 2026", w/ English Translation, 9 pgs.
"Chinese Application Serial No. 202211285624.3, Request for Reexamination filed Jan. 12, 2026", w/ English Claims, 15 pgs.
"Indian Application Serial No. 202244060467, Response filed Oct. 23, 2025 to First Examination Report mailed Sep. 16, 2025", w/ claims, 23 pgs.

* cited by examiner

DELIVERY DEVICES AND METHODS FOR SURGICAL SUBSTANCES

PRIORITY CLAIM

This application claims the benefit of priority to U.S. Provisional Patent Application No. 63/262,850, filed Oct. 21, 2021, and U.S. Provisional Patent Application No. 63/269,069, filed Mar. 9, 2022, the contents of which are hereby incorporated by reference in their entireties.

TECHNICAL FIELD

This document pertains generally, but not by way of limitation, to surgical systems and methods for preparing an anatomic site for surgery. More specifically, but not by way of limitation, the present application relates to systems and methods for delivering substances, such as clotting agents, to a surgical site.

BACKGROUND

Many surgical procedures involve the treatment or removal of target tissue, e.g., diseased, potentially diseased or otherwise unwanted tissue, located inside of a patient. As such, some of these procedures require access to the internal anatomy of the patient via an open procedure or through a smaller opening in minimally invasive (e.g., laparoscopic) procedures. In some endoscopy cases, the patient anatomy is accessed through the mouth or anus. Any other natural orifice as can be used, such as in urology, gynecology, ear-nose-throat (ENT) procedures, without producing an opening or incision in the patient to reach an internal cavity or duct within the patient, such as the gastrointestinal (GI) tract. These endoscopy procedures can be referred to as endolumenal procedures because the procedures take place inside a tube, duct or hollow organ in the body. Some endolumenal procedures involve the removal of tissue from a tissue wall forming the duct or cavity. As such, it can be desirable in these and other applications to administer a clotting agent, such as a hemostat powder, to limit or stop bleeding to, for example, improve visibility within the surgical site for the surgeon and to facilitate healing of the patient.

Overview

The present inventors have recognized, among other things, that problems to be solved in hemostat delivery devices include the difficulty in providing simple to use systems that provide a user-friendly experience. For example, some hemostat materials comprise liquids that are delivered with difficult-to-use, manually operated syringes. Some hemostat powder delivery systems operate with a pump that is located at the hospital or facility at which the procedure is performed. However, such pumps require a large initial expenditure by the procedure provider. Some hemostat delivery systems operate using pressurized air or CO2 provided by the facility. However, the pressures at which these gases operate can fluctuate based on building conditions, such as how much of the gas other functions of the facility are using at the time of the procedure. Additionally, other handheld hemostat powder delivery devices utilize compressed gas cartridges that provide pressurized gas over a wide range of pressures. For example, the cartridge can provide an initially high pressure that gradually tapers off as propellant in the cartridge diminishes. The initially high pressure can often be too high, resulting in excessive spray of the hemostat powder onto areas where it is not intended to reach, such as anatomy away from the bleeding or a scope being used in the procedure, thereby potentially obstructing lenses and lumens of the scope. Additionally, the present inventors have recognized that even with the use of a pressure limiting valve, the performance of the compressed gas canister still diminishes over time and provides an inconsistent user experience.

In summary, two major issues persist with the use of pressurized gas cartridges for delivery of clotting agents, such as hemostat powder: 1) The initial pressure can be too high causing powder to fill the lumen of the anatomy and loss of visibility due to powder being dispersed in the air and obstructing lenses (which physician refers to as a "white-out"); and 2) the powder can attach itself to places that it is not intended to attach such as the endoscope or areas of the bowel that do not need to be treated. The present inventors have recognized that, as the pressure in the propellant cartridge reduces, the physician can have better control and can direct the hemostat to the appropriate area, but the continuously decreasing pressure can affect a consistent user experience. Thus, the present inventors have recognized that it is desirable for a hemostat delivery device to provide a consistent pressure over a period of time to allow for delivery at an appropriate level in a predictable manner.

The present subject matter can provide solutions to these problems and other problems, such as by providing surgical substance delivery devices, such as hemostat powder delivery devices, that provide a cost-effective, user-friendly experience. In particular, the present subject matter can provide a hemostat delivery system that can deliver hemostat material, such as a powder, via pressurized gas at a constant or near constant pressure, which thereby eliminates or reduces the "white-out" effect and reduces instances of the powder attaching to unintended or undesirable locations. The delivery pressure can be set below where white out conditions occur and at a level so that the propellant cartridge can deliver consistent dispensing over a prolonged period of time where the user intends the substance to be delivered.

An example solution of the present disclosure comprises a single-use, all-in-one package that delivers hemostat powder at a constant or near constant flow. The present disclosure provides a low-cost method to automatically maintain the pressure of the gas within the handle. For example, a constant flow valve can be used. A constant flow valve can comprise a spring-loaded diaphragm that enables a constant outflow regardless of the pressure of the incoming flow. An optional adjustment screw can be added to allow the user to adjust the outflow pressure.

In an example, a clotting agent delivery system can comprise a frame, a passageway extending at least partially along the frame, a discharge opening connected to the passageway, a clotting agent reservoir fluidly connected to the passageway to hold a volume of a clotting agent substance, a valve positioned in the passageway to control flow of clotting agent substance through the passageway, and an actuator for selectively allowing propellent to flow into the passageway, wherein the valve and the clotting agent reservoir cooperate to provide clotting agent substance to the discharge opening at a constant pressure using the propellant.

In an additional example, a method for delivering a clotting agent can comprise inserting a delivery catheter into an anatomic area, coupling a clotting agent delivery system to the delivery catheter, the clotting agent delivery system having a reservoir of a clotting agent, operating a valve to release propellant for propelling the clotting agent, and conveying the propellant and the clotting agent to the delivery catheter at a constant pressure.

This overview is intended to provide an overview of subject matter of the present patent application. It is not intended to provide an exclusive or exhaustive explanation of the invention. The detailed description is included to provide further information about the present patent application.

Figure 1:
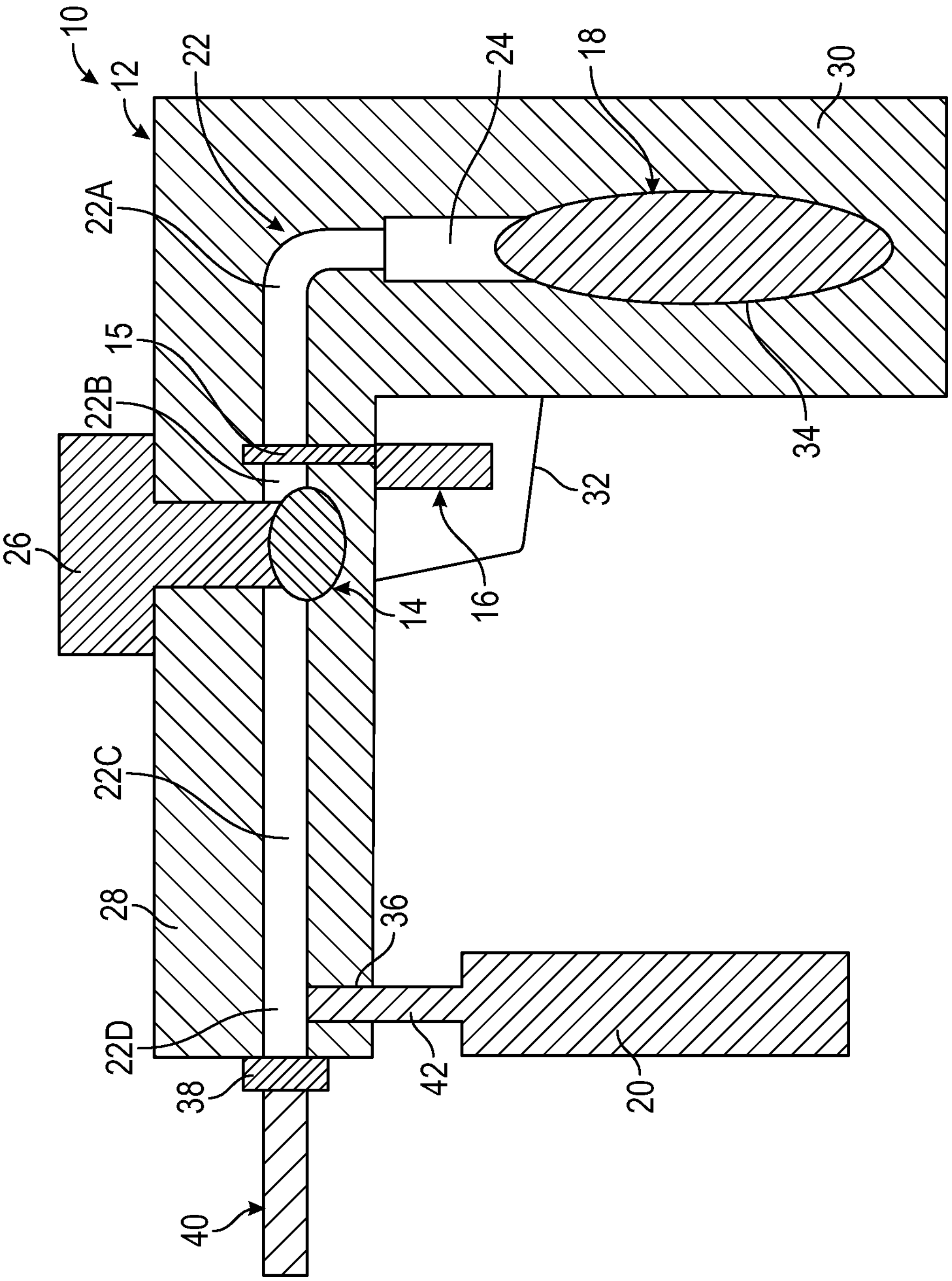
FIG. 1 is a schematic illustration of a substance delivery device configured to deliver hemostat powder at a consistent pressure.

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

DETAILED DESCRIPTION

FIG. 1 is a schematic illustration of substance delivery device 10 configured to deliver hemostat powder at a consistent pressure. Substance delivery device 10 can comprise frame 12, pressure control valve 14, flow valve 15, actuator 16, propellant cartridge 18, substance reservoir 20, fluid passageway 22, cartridge socket 24 and operator control 26. Frame 12 can comprise dispensing portion 28, handle 30, guard 32, cartridge receptacle 34, reservoir socket 36 and injection coupler 38.

Substance delivery device 10 can be configured to deliver clotting agents such as hemostat powder, as well as other substances, at a controlled and consistent pressure. Clotting agents can comprise granules of one or more of a mineral, such as zeolite, a chitosan and starch-based materials. Commercially available clotting agent powders can be utilized with substance delivery device 10. In examples, substance delivery device 10 can deliver hemostat powder at a constant pressure. In examples, substance delivery device 10 can comprise a single-use device that is contained as a single, handheld unit.

Substance delivery device 10 can comprise frame 12 having handle 30 and dispensing portion 28. From an ergonomics perspective, handle 30 and dispensing portion 28 can be arranged in a pistol-like configuration. Actuator 16 can be configured as a trigger and can extend from dispensing portion 28 proximate handle 30. Actuator 16 can be partially bounded by guard 32 that extends from dispensing portion 28 to handle 30 to prevent accidental or unintended activation of actuator 16.

Passageway 22 can extend through, or be attached to, portions of one or both of dispensing portion 28 and handle 30 to fluidly connect propellant cartridge 18 with injection coupler 38. In examples, passageway 22 can comprise one or more lengths of tubing, conduit, piping and the like. In examples, passageway 22 can comprise tunnels or bores extending through material of dispensing portion 28 and handle 30.

First portion 22A of passageway 22 can extend from socket 24 for cartridge 18 to valve 15. First portion 22A, such as a first end of passageway 22, can include socket 24 that allows fluid coupling between propellant cartridge 18 and passageway 22. Socket 24 can engage propellant cartridge 18 in a sealable fashion such that propellant within propellant cartridge 18 can enter passageway 22 without leakage. In examples, socket 24 can comprise a threaded coupler.

Second portion 22B of passageway 22 can extend from valve 15 to valve 14. Second portion 22B of passageway 22 can fluidly connect valve 15 and valve 14 in any suitable manner.

Third portion 22C of passageway 22 can extend from valve 14 to substance reservoir 20. Third portion 22C of passageway 22 can fluidly connect valve 14 and substance reservoir 20 in any suitable manner.

Fourth portion 22D, such as a second end of passageway 22, can include coupler 38 that allows fluid coupling between passageway 22 and deliver device 40. In examples, coupler 38 can comprise a threaded coupler or a barbed hose fitting. Fourth portion 22D of passageway 22 can extend from substance reservoir 20 to injection coupler 38 for delivery device 30, such as a catheter, tube or another instrument or component for directing the substance of substance reservoir 20 into anatomy of a patient. In examples, delivery device 30 can be configured for use in endoluminal procedures. In the case of endoluminal procedures and others, delivery device 40 can comprise a catheter that can be inserted into the working channel of an endoscope having one or more of imaging, lighting, irrigating, steering and navigation capabilities, as well as other features that are known in the art. Endoluminal procedures can involve accessing the patient anatomy through the mouth or anus, as well as any natural orifice as can be used in urology, gynecology, ear-nose-throat (ENT) procedures, without producing an opening or incision in the patient to reach an internal cavity or duct within the patient, such as the gastrointestinal (GI) tract. These endoscopy procedures can be referred to as endoluminal procedures because the procedures take place inside a tube, duct or hollow organ in the body. Some endoluminal procedures can involve the removal of tissue from a tissue wall forming the duct or cavity and can benefit from the application of clotting agents. Examples of procedures that can be performed with the present disclosure include Polypectomy, Endoscopic Mucosal Resection (EMR), and Endoscopic Submucosal Dissection (ESD), which are used to remove tissue within the Gastro-Intestinal (GI) tract, and Full-Thickness Resection (FTR) and endoscopic ultra-sound (EUS) drainage using a stent.

Valve 15 can be positioned in or connect different portions of passageway 22. As discussed herein, valve 15 can be operated to allow flow of propellant in propellant cartridge 18 to valve 14 and eventually substance reservoir 20. Valve 15 can provide propellant from propellant cartridge 18 to valve 14, such as at the pressure that propellant cartridge 18 provides the propellant. Valve 15 can comprise an on-off valve that operates in two states: opened and closed. Valve 15 can be operated via actuator 16, which can comprise a trigger or button. In examples, actuator 16 can simply activate valve 15 between the open and closed positions. Valve 15 can act as a gateway for propellant from propellant cartridge 18 that can be opened by a user when desired. Actuator 16 can be connected to valve 15 via appropriate linkages to allow a user to selectively open and close valve 15 to dispense substance from substance reservoir 20 using the propellant. In examples, actuator 16 can additionally or alternatively operate a spray nozzle for substance delivery device 10, as discussed with reference to FIGS. 4A and 4B, to allow the user to control volumetric flow of the substance, for example.

Valve 14 can comprise a pressure control valve or another device that can both 1) limit the maximum pressure provided to substance reservoir and 2) maintain the pressure provided from propellant cartridge 18 at a steady level. In examples, valve 14 can comprise a constant pressure device wherein variable pressure propellant entering valve 14 can be discharged at a constant or near constant pressure. Valve 14 can comprise a gas regulator constructed as described with reference to FIG. 3. In examples, valve 14 does not interrupt, e.g., shut-off, flow of propellant from valve 15, but allows the propellant to pass therefrom at a regulated pressure. In additional examples, valve 14 can comprise an electronically controlled valve, as discussed in greater detail with reference to FIG. 2. In examples, valve 14 can comprise an inflatable balloon or bladder as described with reference to FIGS. 6A and 6B. Actively or electronically controlled valves and inflatable balloons and bladders can act as variable constrictions to control backpressure within passageway 22. Operator control 26 can be connected to valve 14 and can be adjusted to control the volume or pressure of propellant entering substance reservoir 20. In examples, operator control 26 can be omitted and valve 14 can be set to provide a single pressure output.

Substance reservoir 20 can be connected to fluid passageway 22 at reservoir socket 36 via inlet 42. Substance reservoir 20 can comprise a canister or container configured to hold a substance or material to be dispensed by substance delivery device 10. In examples, the substance or material can comprise solid granules or a liquid, or solid granules suspended in a liquid. In examples, substance reservoir 20 can hold a hemostat powder or another clotting agent. Reservoir socket 36 can provide a coupling point for substance reservoir 20 that allows propellant to enter substance reservoir 20 and substance in substance reservoir 20 to enter passageway 22. In examples, inlet 42 can be configured to receive propellant from propellant cartridge 18 in third portion 22C and provide substance of substance reservoir 20 to fourth portion 22D, as explained herein. In examples, propellant can be used to positively displace or push substance within substance reservoir 20. In examples, propellant within passageway 22 can gather substance from substance reservoir 20 via Bernoulli action. In examples, substance reservoir 20 can be directly pressured with a pressurized propellant, such as an aerosol, as is described in greater detail with reference to FIG. 5.

In examples, propellant cartridge 18 can comprise a compressed gas cartridge. Propellant cartridge 18 can be removable from frame 12 to allow a user to replace propellant cartridge 18 with another propellant cartridge after propellent is depleted. In examples of substance delivery device 10 that are configured to be disposable, propellant cartridge 18 can be concealed and locked within frame 12 such at a user does not have ready access to propellant cartridge 18. However, propellant cartridge 18 can be accessed within handle 30 via removable panel or the like to allow a user to easily replace propellant cartridge 18. Passageway 22 can fluidly couple propellant cartridge 18 to valve 14. In examples, flow of propellant from cartridge 18 is unregulated by propellant cartridge 18 such that propellant flow from propellant cartridge 18 initially at a high, maximum pressure that gradually diminishes to a low, or minimum pressure while valve 15 is open, eventually dropping to zero pressure or atmospheric pressure as the propellant is spent. As discussed herein, substance delivery device 10 can be configured to control the pressure from propellant cartridge 18 to provide a steady volume or pressure of propellant to substance reservoir 20, thereby providing the substance at a suitable pressure level that avoids white out conditions and at a steady pressure level or levels that allow the user to direct the pressure onto target anatomy in a predictable manner.

Valve 14 can control the passage of propellant from propellant cartridge 18 to substance reservoir 20 when valve 15 is open. Operator control 26 can be connected to valve 14 to allow a user to control the discharge pressure of valve 14. In examples, valve 14 can be automatically activated by pressures within substance delivery device 10 relative to ambient pressure. Valve 14 can be configured to maintain the pressure of propellant provided to substance reservoir 20 at a constant or near constant pressure. A pressure regulating valve suitable for use in substance substance delivery device 10 of FIG. 1 can comprise any know valve capable of receiving a gas at different inlet pressures and discharging the gas at a constant pressure. Pressure control valve 14 can comprise a gas pressure regulator. Examples of gas pressure regulators are used to regulate gas or propane in lines of residential homes and take the variable pressure from the tank or line coming into the house and provide a constant pressure to the appliance it feeds. Thus, valve 14 can be configured to receive variable pressure gas from propellant cartridge 18 and discharge the propellant at a constant pressure.

In examples, an unregulated pressurized gas or propellant can flow into valve 14 at the supply pressure provided by propellant cartridge 18, which may vary. As discussed in greater detail with reference to FIG. 3, the supply pressure can be contained in a first chamber (e.g., at surface 104 of FIG. 3) having outflow controlled by pressure control valve 14, which can be connected to a spring (e.g., spring 122 of FIG. 3) that can regulate the discharge pressure. Pressurized gas can leave the first chamber through pressure control valve 14 to a second chamber (e.g., chamber 98 of FIG. 3). The second chamber can have a gas outlet to flow into substance reservoir 20. The pressure of the gas in the second chamber can be adjusted to the desired constant outflow pressure by the spring. In examples, the user can adjust tension in the spring to adjust the constant outflow pressure, such as by adjustment of operator control 26.

Figure 2:
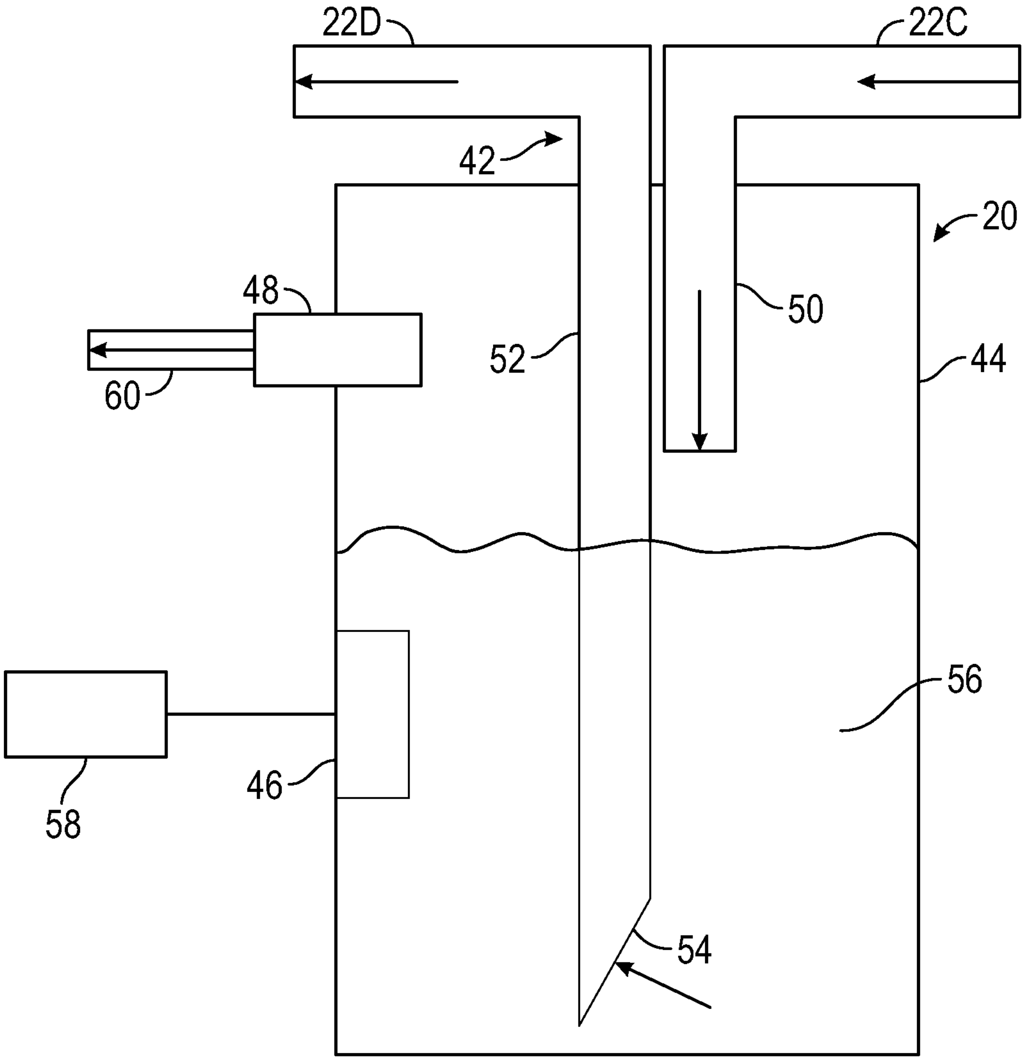
FIG. 2 is a schematic view of a reservoir for storing substance to be dispensed by the substance delivery device of FIG. 1.

FIG. 2 is a schematic view of substance reservoir 20 for storing material to be dispensed by substance delivery device 10 of FIG. 1. Substance reservoir 20 can include inlet 42, canister 44, pressure sensor 46 and valve 48. Inlet 42 can comprise propellant discharge port 50 and substance discharge port 52. Propellant discharge port 50 can be connected to third portion 22C of passageway 22. Substance discharge port 52 can be connected to fourth portion 22D of passageway 22. Substance discharge port 52 can include inlet 54 to receive substance 56 within canister 44. Pressure sensor 46 can be connected to controller 58. Valve 48 can include outlet 60. In examples, clotting agents suitable for use as substance 56 are described in Khoshmohabat, Hadi et al. "Overview of Agents Used for Emergency Hemostasis." Trauma monthly vol. 21,1 e26023. 6 Feb. 2016, doi: 10.5812/traumamon.26023. In examples, substance 56 can comprise a commercially available hemostat.

Canister 44 can comprise any suitable container for holding hemostat powder and other substances. Canister 44 can be fabricated from glass, plastic or metal. Canister 44 can be clear or transparent to allow for viewing of the amount of substance within canister 44. Canister can include hash marks, a scale or graduated markings to provide an indication of the level of substance within canister 44. Canister 44 can be attached to frame 12 (FIG. 1) in any suitable manner. In examples, canister 44 can be threaded into engagement with frame 12. In examples, the top end of canister 44 can be open to allow for filling or adding of substance to canister 44, with the opening being closed and sealed when engaged with frame 12. In additional examples, canister 44 can be enclosed except for a sealed receptacle into which inlet 42 can be inserted.

Inlet 42 can connect the interior of canister 44 with passageway 22. In the illustrated example, inlet 42 can comprise discharge port 50 connecting to third portion 22C and discharge port 52 connecting to fourth portion 22D. Thus, in examples, third portion 22C and fourth portion 22D can be fluidly separated by canister 44. Third portion 22C can provide pressurized propellant, at the pressure level determined by valve 14, to discharge port 50. Discharge port 50 can provide propellant to the headspace within canister 44 above substance 56, thereby pushing substance 56 downward (relative to the orientation of FIG. 2). Pressurized substance 56 can be pressurized to the same pressure as the propellant. Pressurized substance 56 can be pushed into inlet 54 of discharge port 52. Inlet 54 can be angled or oriented to facilitate pressurized substance 56 being pushed into discharge port 52. Pressurized substance 56 can enter discharge port 52 and continue into fourth portion 22D of passageway 22, further flowing out of substance delivery device 10 and into catheter 40 (FIG. 1).

In examples of substance reservoir 20, discharge ports 50 and 52 can be replaced with an opening and third portion 22C can be directly linked to fourth portion 22D. Thus, substance 56 can be configured to be pulled into flow of propellant in passageway 22 via Bernoulli effect.

Pressure within canister 44 can be controlled by pressure of propellant flowing into canister 44, as mentioned, such as at the pressure determined by valve 14. Pressure within canister 44 can additionally or alternatively be controlled using one or both of pressure sensor 46 and valve 48. Pressure sensor 46 can be configured to sense the pressure within canister 44. Pressure sensor 46 can be positioned toward the bottom end of canister 44 so as to be within substance 56, as illustrated. Alternatively, pressure sensor 46 can be provided in the headspace within canister 44 above substance 56. In additional examples, multiple pressure sensors can be used, such as within and above substance 56. In the various configurations, pressure sensor 46 can obtain a pressure measurement reading of the pressure within canister 44 and provide the reading to controller 58. Controller 58 can be electronically connected to valve 14 of FIG. 1 and pressure sensor 46. In such examples, valve 14 can comprise an electrically operated valve that can be opened or closed based on output of sensor 46. In examples, valve 14 can comprise an on-off valve that can be pulse width modulated, e.g., the amount of time valve 14 is opened can be controlled in short bursts to control pressure in third portion 22C. In examples, valve 14 can comprise a variable valve that can be partially opened in different at different levels (e.g., the flow area can be varied) to control pressure in third portion 22C. The length of time valve 14 is left opened or the amount that valve 14 is opened can be related to the pressure reading of sensor 46 to maintain the pressure within canister 44 at a desired pressure. The desired pressure can be set by controller 58 below levels at which white out conditions occur and at levels where the user can apply hemostat powder at suitable velocities or volumes.

Valve 48 can comprise a relief valve or vent valve configured to vent canister 44 at elevated pressures. In examples, valve 48 can open at pressure close to where white out conditions occur, before white out conditions can occur. In examples, valve 48 can simply vent to the atmosphere. Valve 48 can be automatically operated via spring pressure or can be electronically connected to controller 58 to be actuated based on output of pressure sensor 46. In examples, valve 48 can be connected to outlet 60. Outlet 60 can comprise a conduit, e.g., a tubing, connecting back to portion 22C of passageway 22, thereby preserving propellant. In examples, valve 48 can operate without valve 14 or sensor 46. Thus, valve 48 can provide a simple way to avoid white out conditions without actively controlling pressure within canister 44 with a control valve or an electronically modulated valve, etc. However, valve 48 can be used with any of the pressure controlling or modulating components described herein as a back-up.

In the various examples, described herein, substance delivery device 10 can be provided with power, such as via an internal power source comprising a battery, to power controller 58, pressure sensor 46 and valve 48.

Figure 3:
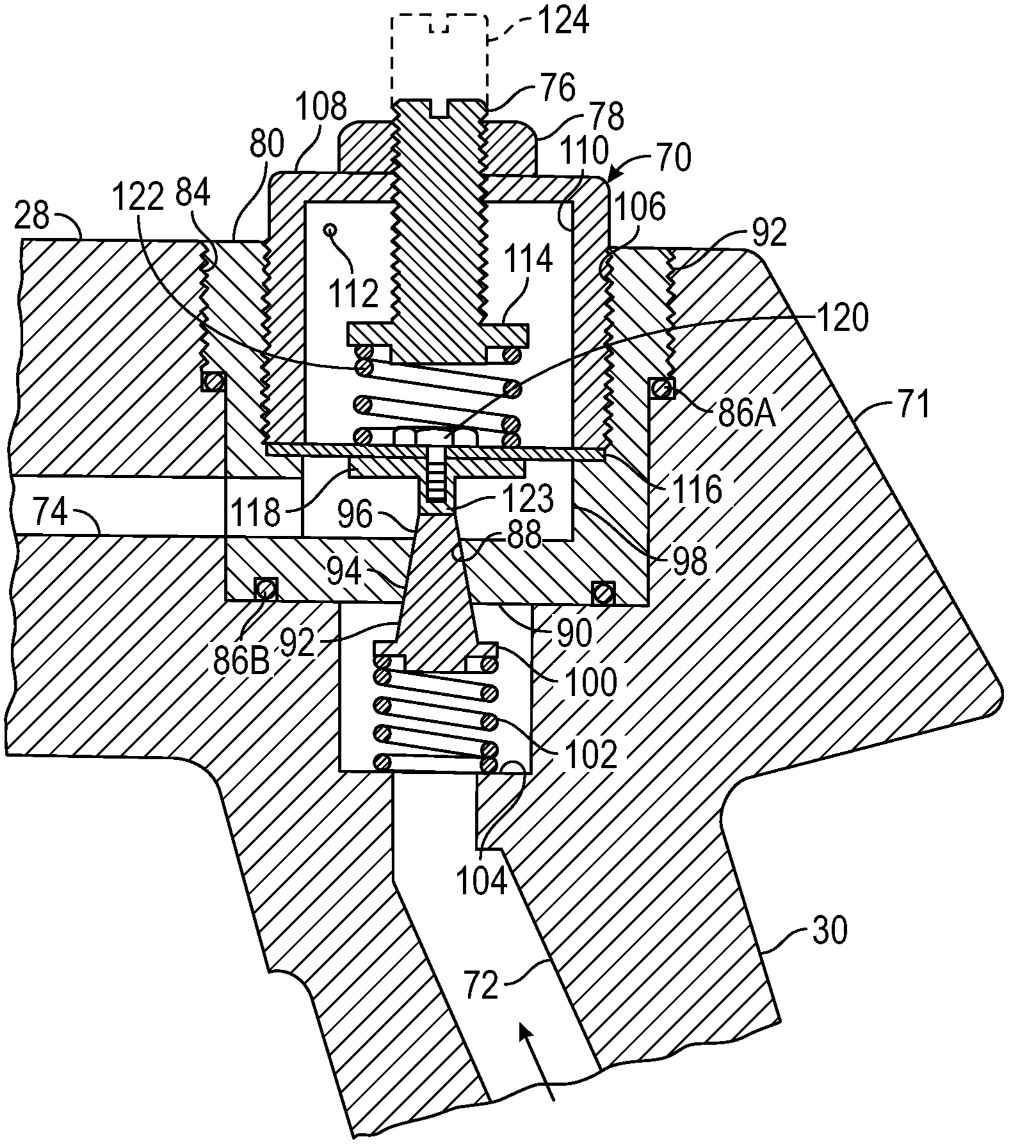
FIG. 3 is a cross-sectional view of a constant flow valve suitable for use with the substance delivery device of FIG. 1.

FIG. 3 is a cross-sectional view of valve 70 suitable for use with substance delivery device 10 of FIG. 1. Valve 70 can comprise an example of valve 14 (FIG. 1). Valve 70 can be located in housing 71 between the passages 72 and 74. Housing 71 can comprise frame 12 (FIG. 1) and passages 72 and 74 can comprise portions 22B and 22C of passageway 22 (FIG. 1), respectively.

Valve 70 can include a controlled variable orifice which drops the high pressure of propellant received from passage 72 to a predetermined constant pressure of no greater than a pre-set limit for delivery through passage 74 to coupler 38 (FIG. 1). Screw 76 on valve 70 can permit a user of substance delivery device 10 to adjust the pre-set pressure delivered to passage 74. Screw 76 can comprise an example of operator control 26. Once adjustment screw 76 is set, jam nut 78 can be tightened to prevent accidental changes in the set pressure. If desired, a scale can be marked on screw 76 to indicate the air pressure established by the different settings of screw 76. Valve 70 can maintain the set air pressure delivered to passage 74 during changes in pressure at passage 72 due to, for example, varying charge levels in propellant cartridge 18. In examples, the pressure provided by propellant cartridge 18 (FIG. 1) can start out at approximately 800 pounds per square inch (psi) (~5.5 Mega-Pascals [MPa]), and valve 70 can be adjusted to limit the pressure in the range of approximately 600.0 psi (~4.1 Mpa) and approximately 200.0 psi (~1.4 MPa).

Valve 70 can have body 80 having external threading 82 for engaging threading on opening 84 in housing 71. O-rings 86A and 86B can form airtight seals between housing 71 and valve body 80. Tapered valve seat 88 can be formed in lower surface 90 of valve body 80. Valve seat 88 can be tapered to open towards passage 72. Valve needle 92 can have conical section 94 seated on valve seat 88. Valve needle 92 can have end 96 that projects through valve seat 88 into chamber 98 in valve body 80. Chamber 98 can connect through valve body 80 to passage 74. Head 100 can be formed on an end of valve needle 92 opposite end 96. Bias spring 102 can be compressed between head 100 and surface 104 in housing 71. Both of spring 102 and the pressure of the propellant in passage 72 can act on valve needle 92 to urge valve needle 92 against valve seat 88 to close valve 70.

Valve body 80 can have internally threaded opening 106. Cap 108 can have external threading configured to mate with threading on opening 106 to form chamber 110. Vent 112 can be provided through cap 108 to maintain chamber 110 at ambient pressure. Screw 76 can be threaded through cap 108 and extend into chamber 110, where it can terminate at an enlarged diameter head 114. Resilient diaphragm 116 can be clamped between cap 108 and valve body 80 to separate chambers 110 and 98. At the center of diaphragm 116, diaphragm retainer 118 can be located in chamber 98. Fastener 120 can be located in chamber 110 and extend through the center of diaphragm 116 and to engage retainer 118 to secure retainer 118 to diaphragm 116. Retainer 118 can have central projection 123 which can abut valve needle end 96. Pressure control spring 122 can be located in chamber 110 and can be compressed between head 114 on adjustment screw 76 and diaphragm 116 to press central projection 123 against valve needle end 96.

In operation, pressure control spring 122 can exert a greater pressure on valve needle 92 than does the combined forces of needle bias spring 102 and the gas pressure in passage 72. Consequently, valve needle 92 can be moved away from seat 88 to create a relatively large annular orifice. Gas can flow from passage 72 through the open orifice into chamber 98. Gas entering chamber 98 can flow through passage 74 to substance reservoir 20. Initially, valve needle 92 can separate from seat 88 to form a relatively large annular orifice. Consequently, gas pressure can build up in chamber 98 and at substance reservoir 20. As the gas pressure builds up in chamber 98, it can act against diaphragm 116. When the pressure on diaphragm 116 becomes sufficient, diaphragm 116 can move and valve needle 92 correspondingly can be moved by spring 102 to decrease the size of the annular orifice. Accordingly, the position of valve needle 92 is automatically adjusted to maintain a constant pressure in the chamber 98 and, hence, a constant pressure at substance reservoir 20. Because of the pressure drop due to the restricted size of the annular orifice, there can be a corresponding volume increase to the lower pressure gas flowing into chamber 98. As flow requirements at substance reservoir 20 change or as the supply pressure changes, the position of valve needle 92 can be changed by diaphragm 116 to maintain the pressure at substance reservoir 20. Adjustment of screw 76 can change the force exerted by spring 122 on diaphragm 116 and consequently can adjust the gas pressure in chamber 98. Spring 122 can be selected to provide the maximum air pressure in chamber 98 of approximately 600 psi (~4.1 MPa) when screw 76 is set to the illustrated position and to provide a minimum air pressure, e.g., 200.0 psi (~1.4 MPa), in chamber 98 when screw 76 is set to the position 124 shown in dashed lines. Spring 122 can be configured to maintain the selected pressure to within +/−5% to maintain a constant or near-constant, but still consistent, pressure.

It will be noted that the design of conical valve needle section 94 and of tapered valve seat 88 provides a relatively large diameter annular orifice when the valve needle 92 is moved from seat 88. This construction can have at least two benefits. First, the annular orifice can be less subject to clogging from any debris in passageway 22. Second, the large diameter permits a relatively large gas flow through valve 70 to provide the high volume of gas desired to supply the relatively large atomization air to substance reservoir 20.

In examples, valve 70 can be constructed similarly to valves described in U.S. Pat. No. 5,284,299, titled "Pressure compensated HVLP spray gun," to Medlock, the contents of which are hereby incorporated herein in their entirety by this reference.

Valve 70 can therefore be configured to limit the pressure at which propellant can enter substance reservoir 20 (FIG. 1) to avoid white out conditions. Furthermore, the pressure of the propellant can be maintained at a steady pressure throughout a substantial portion of the life of propellant cartridge 18 such that the user of substance delivery device can have a consistent user experience. In other words, the total amount of propelling force available by propellant cartridge 18 can be reduced and spread-out so that the propelling force can be evenly distributed over a period of time before eventually falling off as the propellant diminishes, as opposed to immediately and gradually falling off from a very high initial pressure in an unregulated propellant cartridge scenario. Furthermore, propellant cartridges that are only controlled to limit the maximum pressure, e.g., reducing valves, simply reduce the maximum pressure, but still result in an immediate and gradual falling off from the reduced pressure.

Figure 4A:
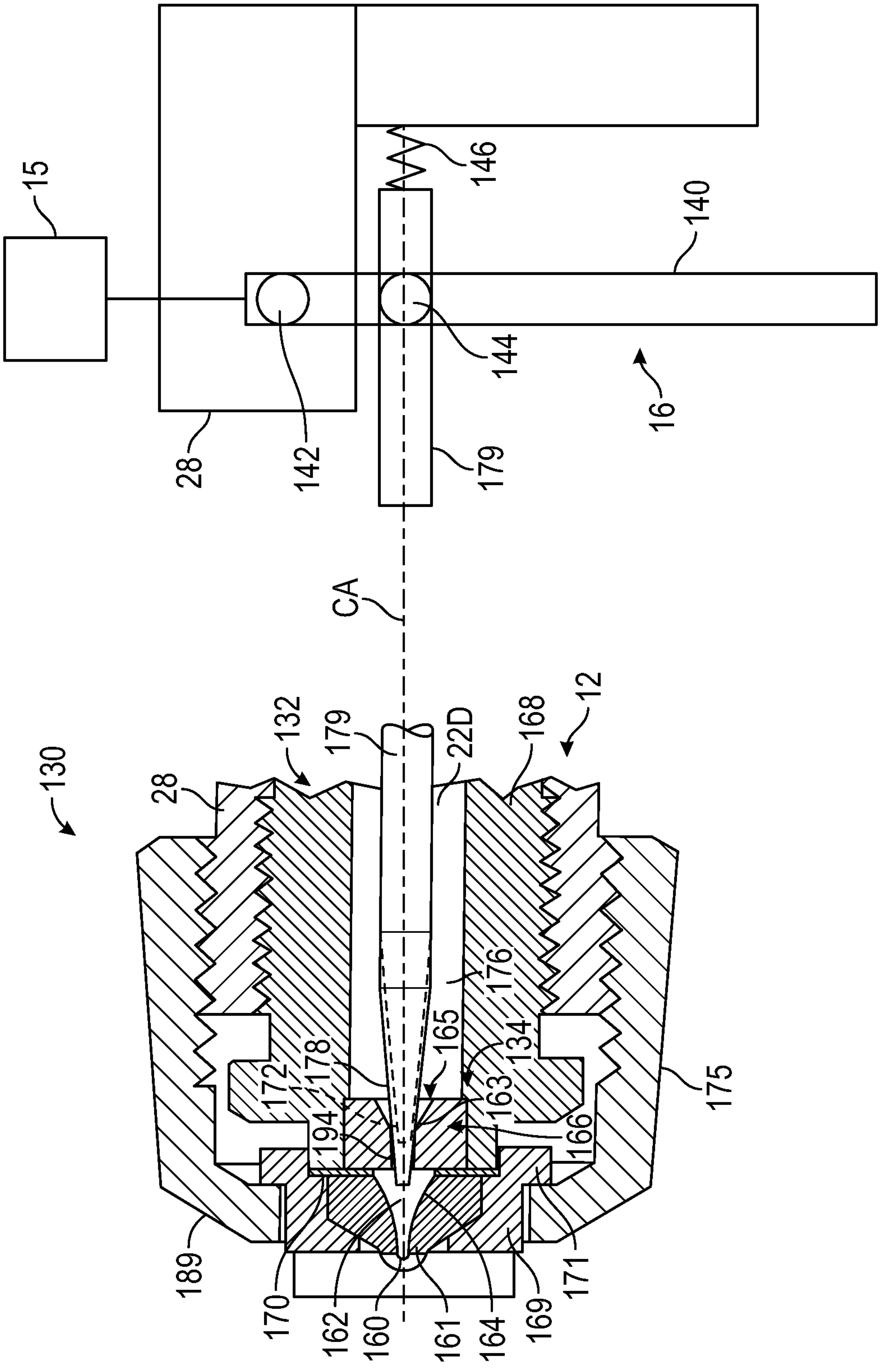
FIG. 4A is a cross-sectional view of a discharge nozzle mechanism and trigger mechanism suitable for use with the substance delivery device of FIG. 1.
Figure 4B:
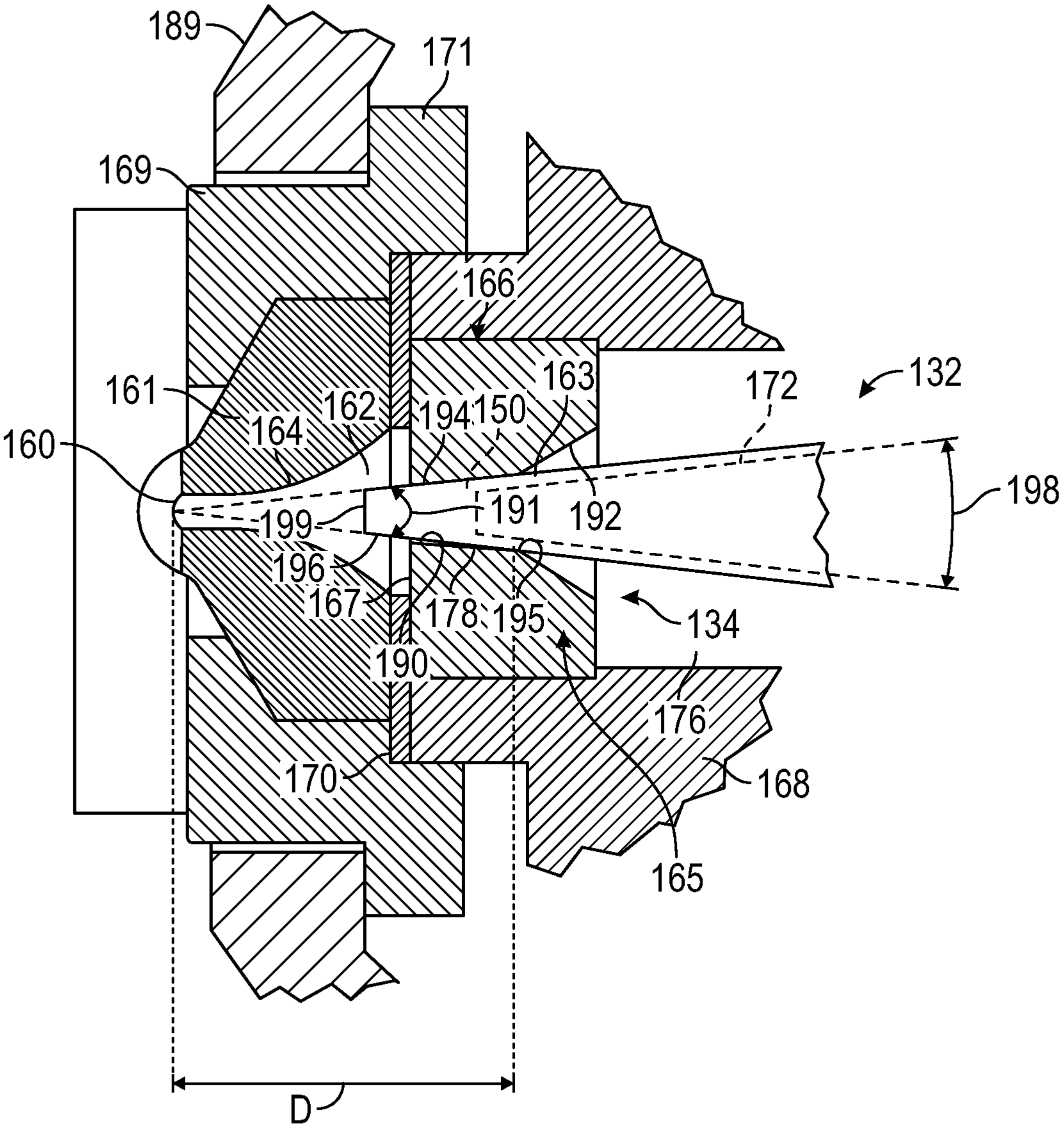
FIG. 4B is a close-up cross-sectional view of a valve needle and valve seat of the discharge nozzle mechanism of FIG. 4A.

FIG. 4A is a cross-sectional view of discharge nozzle mechanism 130 suitable for use with substance delivery device 10 of FIG. 1, wherein discharge nozzle mechanism 130 can comprise valve needle member 132 and valve seat 134. Discharge nozzle mechanism 130 can further comprising spray tip 161 that can be used to shape substance exiting from valve seat 134. FIG. 4B is a close-up cross-sectional view of valve needle member 132 and valve seat 134 of FIG. 4A. FIGS. 4A and 4B are discussed concurrently.

Discharge nozzle mechanism 130 can be located at the forward end of frame 12, at the distal-most end of dispensing portion 28. Spray tip 161, seat member 166, cylindrical member 168 and tip body 169 can be attached to dispensing portion 28 by annular cap 175. Discharge of pressurized substance within fourth portion 22D of passageway 22 can be controlled by engagement of valve needle member 132 and valve seat 134 via operation of trigger 140. Valve needle member 132 and valve seat 134 can operate together as a discharge valve that can control flow of propellant and clotting agent substance from the clotting agent delivery system. Trigger 140 can be mounted to dispensing portion 28 at pivot point 142 and can be pivotably connected to valve stem 179 at pivot point 144. Valve stem 179 can be biased into engagement with valve seat 134 via biasing element 146. Discharge of pressurized substance from fourth portion 22D of passageway 22 can be influenced by spray tip 161, which can have nozzle opening 160 that control the shape of the substance as the substance leaves substance delivery device 10. Trigger 140 can be actuated by a user. Trigger 140 can be connected to flow valve 15 to simultaneously control flow valve 15 and discharge nozzle mechanism 130. The further trigger 140 is retracted to the open position, a larger volume of substance can be dispensed at the pressure determined by valve 14. In other examples, trigger 140 can be used to only control discharge nozzle mechanism 130 and a separate user control can be provided for valve 15.

Spray tip 161 can comprise nozzle opening 160 and pre-nozzle chamber 162. Nozzle opening 160 can be elongated in the direction of axis CA and can penetrate through the forward or distal end surface of spray tip 161. Spray tip 161 can be in communication with pre-nozzle chamber 162. Chamber 162 can have a proximal end with a cross-sectional area substantially greater than that of nozzle opening 160 and tapered side 164 converging in the direction of nozzle opening 160 to funnel substance and propellant gas flowing through valve assembly 165 to nozzle opening 160. The rearward or proximal end of spray tip 161 can abut a portion of seat member 166 and cylindrical member 168 with sealing gasket 170 positioned therebetween, all of which can be secured tightly by tip body 169. Tip body 169 can be in turn held secure by annular cap 175 having internal threads in cooperation with the external threads of dispensing portion 28, and flanged portion 189 engaging shoulder portion 171 of tip body 169. Annular cap 175, and thus spray tip 161, can be easily removed when desired to change to a spray tip with a different size of nozzle opening 160 than spray tip 161 to, for example, change the discharge pattern. Generally, cylindrical member 168 can be positioned immediately to the rear of spray tip 161 and have its forward end abutting spray tip 161 with gasket 170 positioned therebetween. An externally threaded rearward end of cylindrical member 168 can be received into dispensing portion 28. An inner surface of cylindrical member 168 can define axial cavity 176, which can form an extension of fourth portion 22D.

Valve assembly 165 can include seat member 166 held about its periphery in a coaxial relation to nozzle opening 160 by a portion of the inner surface of cylindrical member 168. Tapered, coaxial valve port 194 can be contained in seat member 166 and needle or conical member 178 can be carried by the front end of axially extending valve stem 179. Member 178 can have tapered side 196 (FIG. 4B) converging in the direction of nozzle opening 160 and terminating in one direction at forward end 199 and in the other direction at a point where tapered side 196 intersects with the outer surface of valve stem 179. Forward end 199 of needle member 132 does not converge to a point but rather is terminated to form a substantially flat surface. As can be seen in FIG. 4B, forward end 199 can extend slightly past forward end 167 of seat member 166 when needle member 132 is in a closed position and to the rear of forward end 167 when in an open position. Although the length of needle member 132 from shutoff point 195 to forward end 199 can vary, it can be of sufficient length to form the substance being discharged into an annular cone shaped sheet. Valve stem 179 can be guided by engagement with actuator 16, which in the illustrated example of FIG. 4A comprises trigger 140. Trigger 140 can control movement of valve stem 179 as described herein.

Valve assembly 165 can be arranged so that when trigger 140 is in an advanced position (to the left in FIG. 4A), needle member 132 can be in contact with shutoff point 195 of seat member 166. This can define a closed portion of needle member 132, thereby preventing the substance, under pressure, in axial cavity 176 from flowing through valve port 194. When trigger 140 is moved rearwardly (to the right in FIG. 4A) to a retraced position, valve stem 179 and needle member 132 can be likewise moved rearwardly defining an open position, as designated by dotted line 172 in FIG. 4B, thereby permitting the substance, under high pressure, to flow at a high velocity from axial cavity 176, through cone-shaped passageway 150 between seat member 166 and needle member 132, and through nozzle opening 160 whereby the substance is atomized and sprayed onto the surface to be coated.

Valve port 194, as shown in FIG. 4B, includes tapered seating surface 190, tapered entrance surface 192, and shutoff point 195 located at the intersection of surfaces 190 and 192. Surfaces 190 and 192 can further define two valve port portions each having a shape similar to the frustum of a cone. As shown, seating surface 190 can converge in the direction of nozzle opening 160 with the projected extension converging to a point that can define seat angle 191. Seat angle 191 can facilitate producing the desired spray pattern and can have values in the range of about 9° to about 200 in examples. Likewise, the projected extension of entrance surface 192 can converge and define an entrance angle and can be substantially greater than seat angle 191 in examples. Substance delivery device 10 can operate without entrance surface 192. However, the presence of surface 192 can improve the efficiency of substance delivery device 10 by channeling the high-pressure substance in axial cavity 176 (FIG. 4A) into annular cone-shaped passageway 150 (FIG. 4B) and by allowing for better flow control at shutoff point 195.

As shown in FIG. 4B, tapered side 196 of needle member 132, if extended, can converge in the direction of nozzle opening 160 to define needle angle 198, which can be in the range of about 10° to about 30°, in examples. The value of needle angle 198 in FIG. 4B as compared to seat angle 191 is important in that the two angles are typically not equal to allow for shaping the flow of substance between axial cavity 176 (FIG. 4A) and pre-nozzle chamber 162 and to prevent the locking of needle member 132 when needle member 132 is in a closed position. In addition, greater needle angle allows for the cross-sectional area of the annular cone-shaped passageway 150, located between sealing surface 190 and tapered side 196, to remain relatively constant along its length, when valve assembly 165 is in a selected open position. Thus, the substance flowing through passageway 150 can be maintained at a relatively constant velocity even though the outer diameter of annular cone-shaped passageway 150 can be decreasing in the direction of nozzle opening 160.

In FIG. 4B, distance D is shown to be the distance between nozzle opening 160 and shutoff point 195. The relation between distance D and needle angle 198 facilitates production of the spray pattern for spraying substances. The projected extension of tapered side 196 can converge to a point at or near nozzle opening 160 when needle member 132 is in its closed position, as shown in FIG. 4B. This relationship can allow the substance under high pressure in axial cavity 176 to be accelerated through annular opening 163 between tapered side 196 and shutoff point 195 and to pass through annular cone-shaped passageway 150 causing the substance to be formed into a thin annular cone-shaped sheet which impinges at nozzle opening 160. This impingement, in combination with the increased surface area of annular cone-shaped passageway 150 can produce the desired phenomena at nozzle opening 160 to generate a spray having a uniform spray pattern. In addition, adjustable valve assembly 165 can make it possible for substance passing through annular opening 163 to be accelerated to the velocity at which it will pass through nozzle opening 160. The length of annular cone-shaped passageway 150 between shutoff point 195 and the front end of seat member 166 can also be sufficient in length to form the substance into a thin hollow cone-shaped sheet. A length at least twice the diameter of the orifice opening can be sufficient.

Annular opening 163 can extend completely around needle member 132. When substance flows through opening 163, certain portions of the substance can intersect with other portions so that the impinging force of each portion is equally balanced by the impinging force of one or more other portions. In examples, at least two portions of the substance can converge so that they intersect at nozzle opening 160.

In examples, discharge nozzle mechanism 130 can be constructed similarly to valve assemblies and spray tips described in U.S. Pat. No. 3,633,828, titled "Spray Gun," to Larson, the contents of which are hereby incorporated herein in their entirety by this reference.

Discharge nozzle mechanism 130 of the present disclosure can be configured to allow a user to selectively control the volume of substance discharged from substance delivery device 10. Thus, valves 15 can be used to control on-off flow of the substance, valve 14 can be used to control the pressure of the flowing substance, and discharge nozzle mechanism 130 can be used to control the volume of flowing substance. Valve 14 can control the pressure as described herein so that the user will get a consistent, repeatable experience pulling trigger 16 wherein 1) the same volume of substance comes out at the beginning of the trigger pull each time trigger 16 is pulled and 2) the same volume of substance comes out at the end of the trigger pull each time trigger 16 is pulled, with a constantly increasing amount coming out at the beginning all the way to the end of the trigger pull.

Figure 5:
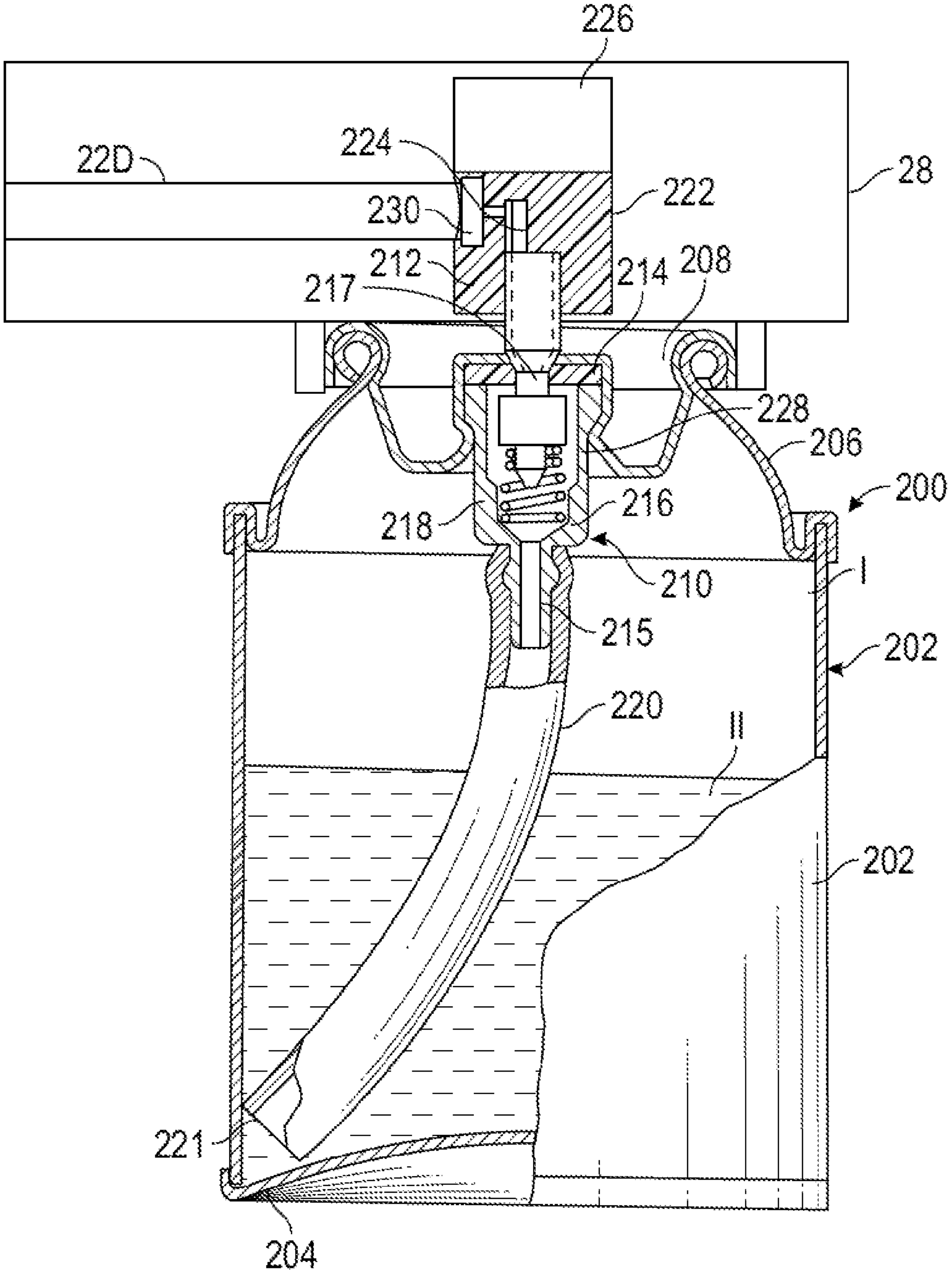
FIG. 5 is a schematic view of a pressurized material reservoir suitable for use with the substance delivery device of FIG. 1.

FIG. 5 is a schematic view of pressurized material reservoir 200 suitable for use with substance delivery device 10 of FIG. 1 as well as other substance delivery devices described herein. Pressurized material reservoir 200 can comprise a self-pressurized container wherein the propellant and the substance to be sprayed are incorporated into a single container. Thus, pressurized material reservoir 200 can replace both of propellant cartridge 18 and substance reservoir 20 of FIG. 1.

Pressurized material reservoir 200 can comprise a two-phase aerosol system comprising container 202, bottom 204, collar 206 and top 208. Valve member 210 can fit into top 208. The contents of container 202 can be divided into two phases, an upper phase I and a lower phase II. Phase II can consist of a liquid phase containing the substance to be dispensed. Phase II can be a propellant which is a vapor under super-atmospheric pressure and in which the substance to be dispensed is dissolved or admixed. Phase I can then be vaporized by the propellant. On the other hand, phase I can be a propellant gas such as CO2 and phase II can be a liquid substance or a liquid having a product dissolved therein. Valve member 210 can comprise hollow stem 212 normally seated against gasket 214 via spring 216. Hollow stem 212 and gasket 214 can engage to form valve 217. Valve body 218 can surround valve stem 212 with tailpiece 215 to which dip tube 220 can be attached. Dip tube 220 can be open at lower end 221.

Valve stem 212 can have actuator or head 222 mounted thereon with passageway 224 therethrough. Head 222 can be depressed by actuator 226 so that hollow stem 212 can be moved downward to open into interior cavity 228 of valve body 218. Since vapor phase I is under super-atmospheric pressure, substance of phase II can be forced into end 221 of dip tube 220 and into passageway 224 when valve 217 is opened to atmospheric pressure, as the expanding vapor of phase I attempts to escape container 202. The liquid of phase II can become vaporized and leave head orifice 230 as a spray. The volume of vapor of phase I can be sufficient to dispense all or substantially all of the liquid of phase II at the same or a similar pressure so that the user receives consistent output every time head 22 is depressed by actuator 226. Thus, pressurized material reservoir 200 can be configured to reduce or eliminate white out conditions. Actuator 226 can be directly coupled to a user control such as actuator 16 (FIG. 1) or can be connected to an electronically controlled actuator that can be operated by a controller, such as controller 58 (FIG. 2).

In examples, pressurized material reservoir 200 can be constructed similarly to pressurized containers described in U.S. Pat. No. 4,546,905 titled, "Aerosol Dispensing System," to Nandagiri et al., the contents of which are hereby incorporated herein in their entirety by this reference.

Figure 6A:
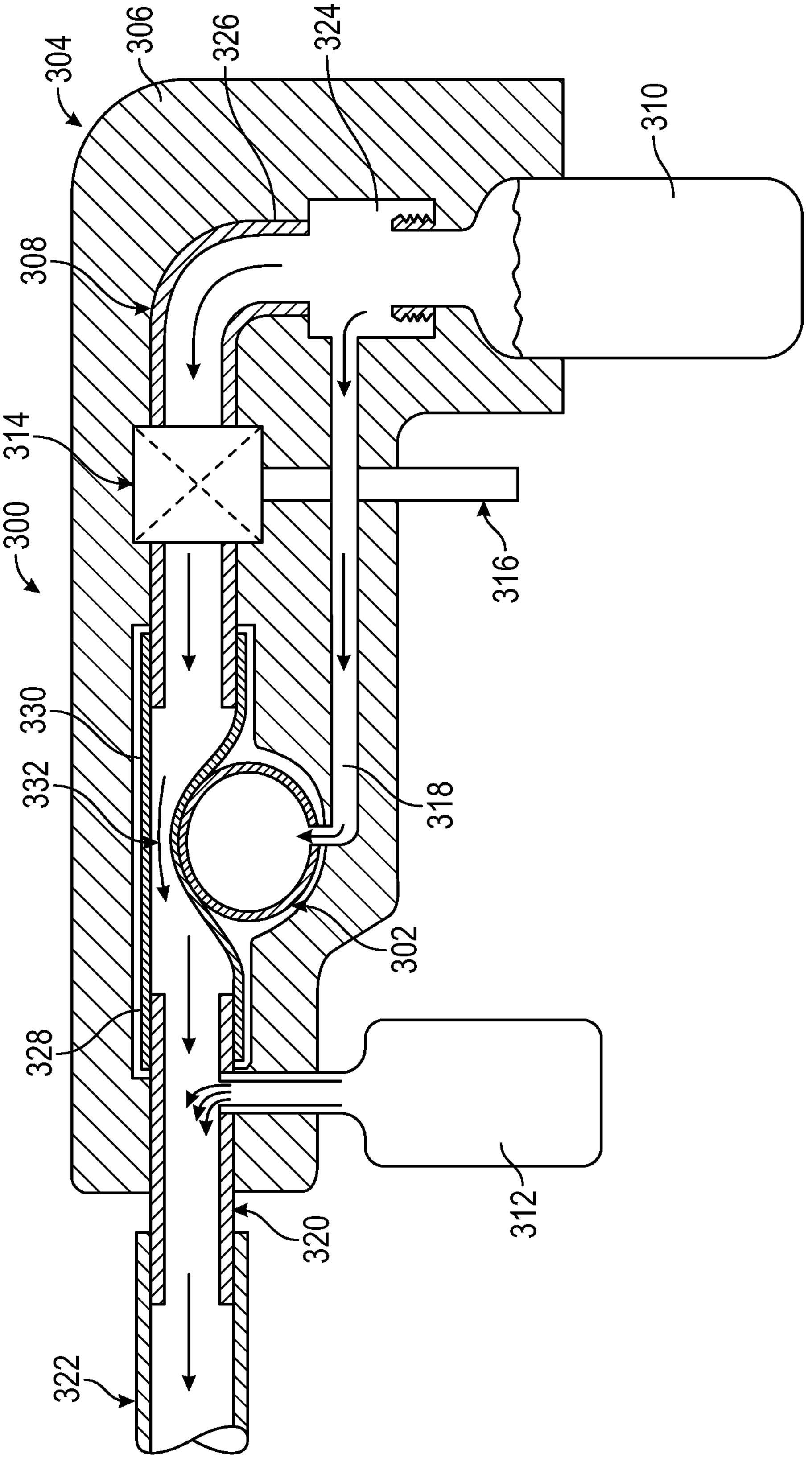
FIG. 6A is a cross-sectional view of a constant pressure flow control apparatus of the present application comprising an inflatable bladder shown in an expanded state.
Figure 6B:
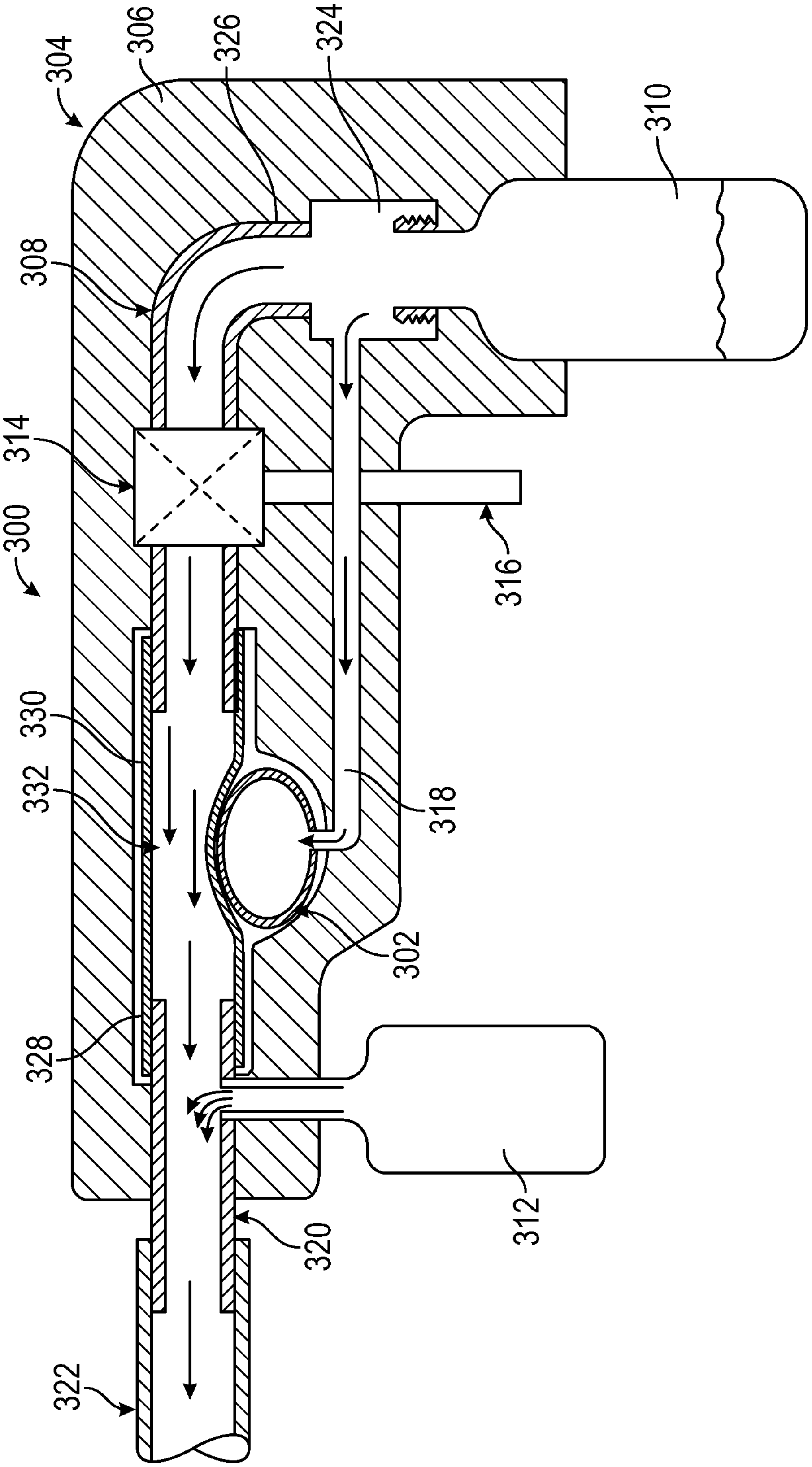
FIG. 6B is a cross-sectional view of the constant pressure flow control apparatus of FIG. 6A with the inflatable bladder shown in a collapsed state.

FIG. 6A is a cross-sectional view of constant pressure flow control apparatus 300 of the present application comprising inflatable bladder 302 in an expanded state. FIG. 6B is a cross-sectional view of constant pressure flow control apparatus 300 of the present application with inflatable bladder 302 in a collapsed state.

Constant pressure flow control apparatus 300 can be used with substance delivery device 304, which can comprise frame 306, passageway 308, propellant cartridge 310, substance reservoir 312, valve 314, actuator 316, inflation conduit 318, coupler 320 and delivery device 322. Constant pressure flow control apparatus 300 can include similar components as substance delivery device 10 of FIG. 1. For example, frame 306 can be configured similarly as frame 12, passageway 308 can extend through frame 306 in a similar manner as passageway 222, coupler 320 can connect to a delivery device similar to coupler 38 and device 40, substance reservoir 312 can be similar to substance reservoir 20, and propellant cartridge 310 can connect to frame 306 similarly as propellant cartridge 18.

Propellant cartridge 310 can be attached to frame 306 in any suitable manner. Propellant cartridge 310 can provide pressurized gas or another propellant to manifold 324. Manifold 324 can be a chamber fabricated in frame 306. Manifold 324 can supply propellant to passageway 308 and inflation conduit 318. Valve 314 can be positioned on passageway 308 to selectively interrupt flow of propellant therethrough via operation of actuator 316. Manifold 324 can provide propellant at the same pressure to passageway 308 and conduit 318. Passageway 308 can be lined with tubing 326, which can extend into chamber 328 in frame 306. Chamber 328 can be lined with flexible tubing 330. Coupler 320 can comprise a tube fluidly coupled to flexible tubing 330. Tubing 326, flexible tubing 330 and coupler 320 can be fluidly connected to provide propellant from manifold 324 to delivery device 322 without, or with minimal, leakage.

Flexible tubing 330 and bladder 302 can be made of material that is stretchable and that can inhibit penetration of gas therethrough, such as rubber. Propellant from propellant cartridge 310 can be provided to bladder 302 via inflation conduit 318. When bladder 302 is deflated or minimally inflated, bladder 302 will not penetrate into chamber 328 and flexible tubing 330 will be at maximum diameter at restriction 332 to allow the largest amount of flow through flexible tubing 330. As bladder 302 becomes increasingly inflated, more of bladder 302 will extend into chamber 328 and flexible tubing 330 will become increasingly constricted at restriction 332 to smaller diameters or sizes to allow decreasing amounts of flow through flexible tubing 330.

Propellant from flexible tubing 330 can be provided to substance reservoir 312. Substance reservoir 312 can be configured to operate similarly as substance reservoir 20 of FIG. 2 and can thus operate to have substance therein displaced by propellent or drawn into a flow of propellant via Bernoulli effect.

Bladder 302 can be inflated at the same pressure as propellant cartridge 310 and can thereby mimic the same pressure curve as propellant cartridge 310 for the life of the propellant. For example, bladder 302 can first be initially inflated at a high pressure that gradually tapers off as propellant in propellant cartridge 310 is consumed or discharged. Bladder 302 can become immediately pressurized when a pressurized propellant cartridge 310 is connected to frame 306. However, an additional valve can be provided on inflation conduit 318 to independently inflate bladder 302. Such a valve can be independently operated from valve 314.

In operation, actuator 316 can be moved by a user to open valve 314. Valve 314 can comprise an on-off valve as described herein to allow unregulated pressure from propellant cartridge 310 into flexible tubing 330. As mentioned, propellant from propellant cartridge 310 can be provided to bladder 302 via inflation conduit 318. When propellant cartridge 310 is initially at maximum charge, bladder 302 can be at maximum inflation and can penetrate into chamber 328 the maximum amount for the given charge of propellant cartridge 310. Thus, as a large volume of propellant attempts to escape propellent cartridge, flexible tubing 330 will restrict flow of the propellant, thereby avoiding a large volume of substance being dispensed from substance reservoir 312 and reducing the potential for white out conditions. However, as the pressure of propellant cartridge 310 diminishes, flexible tubing 330 can open up to allow more propellant therethrough. The ratio of propellant pressure at propellant cartridge 310 to the cross-sectional opening of flexible tubing 330 can be inversely proportional. The ratio of propellant pressure at propellant cartridge 310 to the cross-sectional opening of flexible tubing 330 can be configured to be maintained constant, or nearly constant, to provide consistent output of substance from substance reservoir 312.

Constant pressure flow control apparatus 300 can be configured to provide a calibrated balance between bladder 302 that causes a decreasing restriction 332 while having a reduction in pressure from propellant cartridge 310 to maintain constant pressure flow. Constant pressure flow control apparatus 300 can be configured to provide a consistent user experience while avoiding white out conditions without the use of complicated valves or electronic controls. Constant pressure flow control apparatus 300 can provide an easy to manufacture and inexpensive system that can be readily incorporated into single-use devices.

EXAMPLES

Example 1 is a clotting agent delivery system comprising: a frame; a passageway extending at least partially along the frame; a discharge opening connected to the passageway; a clotting agent reservoir fluidly connected to the passageway to hold a volume of a clotting agent substance; a valve positioned in the passageway to control flow of clotting agent substance through the passageway; and an actuator for selectively allowing propellent to flow into the passageway; wherein the valve and the clotting agent reservoir cooperate to provide clotting agent substance to the discharge opening at a constant pressure using the propellant.

In Example 2, the subject matter of Example 1 optionally includes a socket mounted to the frame for receiving a propellant source having the propellant, wherein the valve comprises a constant pressure device in communication with the passageway between the socket and the discharge opening.

In Example 3, the subject matter of Example 2 optionally includes wherein the constant pressure device is adjustable by the user to adjust a level of the constant pressure.

In Example 4, the subject matter of any one or more of Examples 2-3 optionally include wherein the constant pressure device is set at a fixed pressure.

In Example 5, the subject matter of any one or more of Examples 2-4 optionally include wherein the constant pressure device is spring activated.

In Example 6, the subject matter of Example 5 optionally includes wherein the constant pressure device comprises a constant pressure valve comprising: a housing; a diaphragm mounted to the housing to form a chamber; a vent to open the chamber to atmosphere; a first biasing element positioned in the chamber to push against the diaphragm; a valve stem connected to diaphragm opposite the first biasing element, the valve stem positioned in the passageway; a valve seat mounted to the frame, the valve seat positioned within the passageway to receive the valve stem; and a second biasing element configured to push the valve stem into engagement with the valve seat.

In Example 7, the subject matter of any one or more of Examples 2-6 optionally include wherein the constant pressure device is electronically controlled.

In Example 8, the subject matter of Example 7 optionally includes a pressure sensor in the clotting agent reservoir; an electronically activated valve comprising the constant pressure device; and a controller electronically coupled to the pressure sensor and the electronically activated valve to selectively open the electronically activated valve to maintain pressure in the clotting agent reservoir at the constant pressure.

In Example 9, the subject matter of any one or more of Examples 2-8 optionally include wherein the constant pressure device comprises a variable restriction device.

In Example 10, the subject matter of Example 9 optionally includes wherein the variable restriction device comprises an inflatable balloon.

In Example 11, the subject matter of Example 10 optionally includes wherein the variable restriction device further comprises a flexible tube against which the inflatable balloon presses.

In Example 12, the subject matter of any one or more of Examples 10-11 optionally include wherein the constant pressure device further comprises an inflation conduit connecting the propellant source to the inflatable balloon outside of the passageway.

In Example 13, the subject matter of any one or more of Examples 2-12 optionally include wherein the constant pressure device is fluidly coupled to an interior of the clotting agent reservoir outside of the passageway.

In Example 14, the subject matter of Example 13 optionally includes wherein the constant pressure device comprises a relief valve.

In Example 15, the subject matter of any one or more of Examples 2-14 optionally include cartridge.

In Example 16, the subject matter of any one or more of Examples 2-15 optionally include a propellant valve connected to the actuator to control flow of propellant from the propellant source.

In Example 17, the subject matter of Example 16 optionally includes a discharge valve to control flow of propellant and clotting agent substance from the clotting agent delivery system, the discharge valve comprising: an orifice fluidly coupled to the discharge opening; and a needle connected to the actuator to selectively open the discharge orifice.

In Example 18, the subject matter of any one or more of Examples 1-17 optionally include wherein: the clotting agent reservoir includes a volume of clotting agent and a volume of propellant; and the valve is configured to release clotting agent and propellant simultaneously and directly from the clotting agent reservoir into the passageway.

In Example 19, the subject matter of Example 18 optionally includes wherein the clotting agent and the propellant form an aerosol.

In Example 20, the subject matter of any one or more of Examples 1-19 optionally include a catheter couplable to the discharge opening to deliver clotting agent to an anatomic area.

Example 21 is a method for delivering a clotting agent, the method comprising: inserting a delivery catheter into an anatomic area; coupling a clotting agent delivery system to the delivery catheter, the clotting agent delivery system having a reservoir of a clotting agent; operating a valve to release propellant for propelling the clotting agent; and conveying the propellant and the clotting agent to the delivery catheter at a constant pressure.

In Example 22, the subject matter of Example 21 optionally includes wherein: the valve comprises a constant pressure valve; and conveying the propellant and the clotting agent to the delivery catheter at a constant pressure comprises throttling flow of propellant through the valve with a spring-activated diaphragm.

In Example 23, the subject matter of any one or more of Examples 21-22 optionally include wherein: the valve comprises an electronically activated valve; and conveying the propellant and the clotting agent to the delivery catheter at a constant pressure comprises modulating opening of the valve with a controller.

In Example 24, the subject matter of any one or more of Examples 21-23 optionally include wherein: the valve comprises a vent valve in the clotting agent reservoir; and conveying the propellant and the clotting agent to the delivery catheter at a constant pressure comprises venting propellant within the clotting agent reservoir at a threshold pressure below which white out conditions occur.

In Example 25, the subject matter of any one or more of Examples 21-24 optionally include wherein: the valve comprises a variable restriction valve; and conveying the propellant and the clotting agent to the delivery catheter at a constant pressure comprises changing a size of a restriction within the valve.

In Example 26, the subject matter of Example 25 optionally includes wherein the variable restriction valve comprises: a flexible tube through which the propellant flows; and an inflatable bladder connected to a source of the propellant to selectively collapse the flexible tube.

In Example 27, the subject matter of any one or more of Examples 25-26 optionally include wherein the variable restriction valve comprises: an electronically controlled valve; and a controller to selectively adjust a flow path through the electronically controlled valve.

In Example 28, the subject matter of any one or more of Examples 21-27 optionally include wherein: the valve comprises a spray valve; and conveying the propellant and the clotting agent to the delivery catheter at a constant pressure comprises opening the spray valve to simultaneously release propellant and the clotting agent from a pressurized cannister defining the clotting agent reservoir.

In Example 29, the subject matter of Example 28 optionally includes wherein the propellant and the clotting agent are aerosolized by the spray valve.

In Example 30, the subject matter of any one or more of Examples 21-29 optionally include controlling a volume of clotting agent passing into the delivery catheter with a needle valve.

Each of these non-limiting examples can stand on its own, or can be combined in various permutations or combinations with one or more of the other examples.

VARIOUS NOTES

The above detailed description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventor also contemplates examples in which only those elements shown or described are provided. Moreover, the present inventor also contemplates examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A clotting agent delivery system comprising:
- a frame;
- a socket mounted to the frame for receiving a propellant source having a propellant;
- a passageway extending at least partially along the frame;
- a discharge opening connected to the passageway;
- a clotting agent reservoir fluidly connected to the passageway to hold a volume of a clotting agent substance;
- a valve positioned in the passageway to control flow of clotting agent substance through the passageway, wherein the valve comprises a constant pressure device in communication with the passageway between the socket and the discharge opening; wherein the constant pressure device comprises a constant pressure valve comprising:
  - a housing:
  - a diaphragm mounted to the housing to form a chamber;
  - a vent to open the chamber to atmosphere;
  - a first biasing element positioned in the chamber to push against the diaphragm:
  - a valve stem connected to the diaphragm opposite the first biasing element, the valve stem positioned in the passageway;
  - a valve seat mounted to the frame, the valve seat positioned within the passageway to receive the valve stem; and
  - a second biasing element configured to push the valve stem into engagement with the valve seat; and
- an actuator for selectively allowing the propellant to flow into the passageway;
- wherein the valve and the clotting agent reservoir cooperate to provide clotting agent substance to the discharge opening at a constant pressure using the propellant.

2. The clotting agent delivery system of claim 1, wherein the constant pressure device is adjustable by a user to adjust a level of the constant pressure.

3. The clotting agent delivery system of claim 1, wherein the constant pressure device is set at a fixed pressure.

4. The clotting agent delivery system of claim 1, further comprising:
- a pressure sensor in the clotting agent reservoir;
- an electronically activated valve; and
- a controller electronically coupled to the pressure sensor and the electronically activated valve to selectively open the electronically activated valve to maintain pressure in the clotting agent reservoir at the constant pressure.

5. The clotting agent delivery system of claim 1, wherein the propellant source comprises a CO2 cartridge.

6. The clotting agent delivery system of claim 1, further comprising:
- a propellant valve connected to the actuator to control flow of propellant from the propellant source; and
- a discharge valve to control flow of propellant and clotting agent substance from the clotting agent delivery system, the discharge valve comprising:
  - an orifice fluidly coupled to the discharge opening; and
  - a needle connected to the actuator to selectively open the orifice.

7. The clotting agent delivery system of claim 1, wherein:
- the clotting agent reservoir includes a volume of a clotting agent and a volume of a propellant; and
- the valve is configured to release clotting agent and propellant simultaneously and directly from the clotting agent reservoir into the passageway;
- wherein the clotting agent and the propellant form an aerosol.

8. The clotting agent delivery system of claim 1, further comprising a catheter couplable to the discharge opening to deliver clotting agent to an anatomic area.

9. The clotting agent delivery system of claim 1, wherein the actuator controls a flow rate of the propellant passing into the passageway.

10. The clotting agent delivery system of claim 9, wherein the valve is positioned in the passageway downstream of the actuator.

11. A method for delivering a clotting agent, the method comprising:
- inserting a delivery catheter into an anatomic area;
- coupling a clotting agent delivery system to the delivery catheter, the clotting agent delivery system comprising a frame, a passageway extending at least partially along the frame, a discharge opening connected to the passageway, a clotting
  - agent reservoir fluidly connected to the passageway to hold a volume of a clotting agent substance, a valve positioned in the passageway downstream of an actuator to control pressure of clotting agent substance through the passageway, and the actuator for selectively allowing a propellant to flow into the passageway, wherein the actuator is positioned downstream of a propellant source and controls a flow rate of the propellant passing into the passageway;
- operating the valve to release propellant for propelling the clotting agent; and
- conveying the propellant and the clotting agent through the passageway and the discharge opening to the delivery catheter at a constant pressure, wherein the valve and the clotting agent reservoir cooperate to provide clotting agent substance to the discharge opening at the constant pressure using the propellant.

12. The method of claim 11, wherein:
- the valve comprises a constant pressure valve; and conveying the propellant and the clotting agent to the delivery catheter at a constant pressure comprises throttling flow of propellant through the valve with a spring-activated diaphragm.

13. The method of claim 11, wherein:

the valve comprises an electronically activated valve; and conveying the propellant and the clotting agent to the delivery catheter at a constant pressure comprises modulating opening of the valve with a controller.

14. The method of claim 11, further comprising a vent valve in the clotting agent reservoir of the clotting agent; and conveying the propellant and the clotting agent to the delivery catheter at a constant pressure comprises venting propellant within the clotting agent reservoir of the clotting agent at a threshold pressure below which white out conditions occur.

15. The method of claim 11, wherein:

the valve comprises a variable restriction valve; and conveying the propellant and the clotting agent to the delivery catheter at a constant pressure comprises changing a size of a restriction within the valve.

16. A clotting agent delivery system comprising:

a frame;

a passageway extending at least partially along the frame;

a discharge opening connected to the passageway;

a clotting agent reservoir fluidly connected to the passageway to hold a volume of a clotting agent substance;

a valve positioned in the passageway to control pressure of clotting agent substance through the passageway;

an actuator for selectively closing and opening the passageway to allow a propellant to flow into the passageway; and a propellant source mounted to the frame to place propellant in communication with the passageway via the actuator;

wherein the valve and the clotting agent reservoir cooperate to provide clotting agent substance to the discharge opening at a constant pressure using the propellant;

wherein the actuator is positioned in the passageway downstream of the propellant source;

wherein the valve is positioned in the passageway downstream of the actuator; and wherein the actuator controls a flow rate of the propellant from the propellant source passing into the valve.

17. The clotting agent delivery system of claim 16, wherein:

the valve comprises a constant pressure device in communication with the passageway between the propellant source and the discharge opening; and the constant pressure device is adjustable either manually or automatically.

18. A clotting agent delivery system comprising:

a frame;

a passageway extending at least partially along the frame;

a discharge opening connected to the passageway;

a clotting agent reservoir fluidly connected to the passageway to hold a volume of a clotting agent substance;

a valve positioned in the passageway to control pressure of clotting agent substance through the passageway, wherein the valve comprises an electronically-controlled pressure regulating valve;

an actuator for selectively allowing propellant to flow into the passageway, wherein the actuator is configured to operate an on/off valve and the valve is positioned downstream of an actuator;

wherein the valve and the clotting agent reservoir cooperate to provide clotting agent substance to the discharge opening at a constant pressure using the propellant, and wherein the actuator controls a flow rate of the propellant passing into the passageway;

a pressure sensor located in the clotting agent reservoir to directly sense pressure of the clotting agent substance; and a controller electronically connected to the pressure sensor and the valve to selectively open the valve to maintain pressure in the clotting agent reservoir at the constant pressure, wherein the controller is configured to modulate the valve based on feedback from the pressure sensor to maintain the pressure below levels at which white out conditions occur.

* * * * *